US006410335B1

(12) United States Patent
Pollak et al.

(10) Patent No.: US 6,410,335 B1
(45) Date of Patent: Jun. 25, 2002

(54) CIRCULATING INSULIN-LIKE GROWTH FACTOR-I AND PROSTATE CANCER RISK

(75) Inventors: Michael N. Pollak, Montreal (CA); Meir J. Stampfer, Brookline; Edward Giovannucci, Wakefield, both of MA (US)

(73) Assignees: The Brigham and Woman's Hospital, Inc., Boston, MA (US); Sir Mortimer B. Davis - Jewish General Hospital Foundation, Montreal (CA)

( * ) Notice: Subject to any disclaimer, the term of this patent is extended or adjusted under 35 U.S.C. 154(b) by 0 days.

(21) Appl. No.: 09/234,651

(22) Filed: Jan. 21, 1999

Related U.S. Application Data
(60) Provisional application No. 60/072,560, filed on Jan. 21, 1998.

(51) Int. Cl.[7] ............................. G01N 33/48; C12Q 1/00
(52) U.S. Cl. ............................. 436/64; 436/63; 435/4
(58) Field of Search .................. 435/4, 7.1; 436/63, 436/64; 530/399, 350

(56) References Cited

PUBLICATIONS

Finne, P. et al. Insulin–like growth factor I is not a useful marker of prostate cancer in men with elevated levels of prostate–specific antigen. J. Clinical Endocrinology & Metabolism. 85(8):2744–2747, 2000.*
Lash, T.L. Re: Insulin–like growth factor 1 and prostate cancer risk: a population–based, case–control study. J. Natl. Cancer Inst. 90(23): 1841, Dec. 1998.*
Cohen et al., "Cell Proliferation in Carcinogenesis," Science, 249(4972): 1007(5), Abstract Only 1990.
Cohen et al., "Genetic Errors, Cell Proliferation, and Carcinogenesis," Cancer Research, 51: 6493–6505 (1991).
Jones et al., "Insulin–Like Growth Factors and Their Binding Proteins: Biological Actions," Endocrine Reviews, 16(1): 3–34 (1995).
Juul et al., "Serum Insulin–Like Growth Factor–I in 1030 Healthy Children, Adolescents, and Adults: Relation to Age, Sex, Stage of Puberty, Testicular Size, and Body Mass Index," J. of Clinical Endocr. and Metab., 78(3): 744–752 (1994).
Juul et al., "Serum Levels of Insulin–Like Growth Factor (IGF)–Binding Protein–3 (IGFBP–3) in Healthy Children, and Adolescents: The Relation to IGF–I, IGF–II, IGFBP–1, IGFBP–2, Age, Sex, Body Mass Index, and Pubertal Maturation," J. of Clinical Endocr. and Metab., 80(8): 2534–2542 (1995).
Pollak et al., "Effect of Tamoxifen on Serum Insulin–like Growth Factor I Levels in Stage I Breast Cancer Patients," Journal of the Nat. Cancer Instit.,. 82(21): 1693–1697 (1990).

Huynh et al., "A Role for Insulin–Like Growth Factor Binding Protein 5 in the Antiproliferative Action of the Antiestrogen ICI 182780," Cell Growth and Differentiation, 7:1501–1506 (1996).
Huynh et al., "Estradiol and Antiestrogens Regulate a Growth Inhibitory Insulin–like Growth Factor Binding Protein 3 Autocrine Loop in Human Breast Cancer Cells," The Journal of Biological Chemistry, 271 (2): 1016–1021 (1996).
Huynh et al., "Regulation of Insulin–like Growth Factor I Receptor Expression by the Pure Antiestrogen ICI 182780," Clinical Cancer Research, 2:2037–2042 (1996).
Mantzoros et al., "Insulin–like Growth Factor 1 in Relation to Prostate Cancer and Benign Prostatic Hyperplasia," B. J. of Cancer, 76(9): 1115–1118 (1997).
Thissen et al., "Nutritional Regulation of the Insulin–Like Growth Factors," Endocrine Reviews, 15(1):80–101 (1994).
Zarandi et al., "Synthesis and Biological Activities of Highly Potent Antagonists of Growth Hormone–Releasing Hormone," Proc. Natl. Acad. Sci USA, 91:12298–12302 (1994).
Pollak et al., "Rationale for Combined Antiestrogen–Somatostatin Analogue Therapy of Breast Cancer," *Adjuvant Therapy of Cancer VIII*, pp. 145–152 (1997).
Rechler, Editorial: Growth Inhibition by Insulin–Like Growth factor (IGF) Binding Protein–3–What's IGF Got to Do With It?, Endocrinology, 138(7):2645–2647 (1997).
"Prostate Cancer: Progress in Screening, Prevention Holds Promise," Harvard Health Letter, 23(9):4–5 (1998).
Chan et al., "Plasma Insulin–Like Growth Factor–I and Prostate Cancer Risk: A Prospective Study," Science, 279:563–566 (1998).
Cohen, Serum Insulin–Like Factor–I Levels and Prostate Cancer Risk—Interpreting the Evidence, J. of the Nat. Cancer Instit., 90(12): 876–879 (1998).
Wolk et al., "Insulin–Like Growth Factor 1 and Prostate Cancer Risk: a Population–Based, Case–Control Study," J. of the Nat. Cancer Instit., 90(12): 911–915 (1998).
Ho et al., "Insulin–Like Growth Factor–Binding Protein–2 in Patients With Prostate Carcinoma and Benign Prostatic Hyperplasia," Clinical Endocrinology, 46: 333–342 (1997).

(List continued on next page.)

*Primary Examiner*—Anthony C. Caputa
*Assistant Examiner*—Anne L. Holleran
(74) *Attorney, Agent, or Firm*—Haynes and Boone, LLP

(57) ABSTRACT

Methods of predicting a propensity to developing prostate cancer are presented. The consists of measuring the IGF status of individual. Individuals with high IGF status, as compared with normal reference range values, are at increased risk for developing prostate cancer. More particularly, the IGF status may be determined by measuring IGF-I levels and/or IGFBP-3 levels. High IGF and low IGFBP levels are indicative of a high IGF status. A method of determining the prognosis of existing prostate cancers or of monitoring disease progression involves determining the IGF/PSA status of an individual. Individuals with a high IGF/PSA staus (both high IGF status and high PSA levels) tend to develop severe prostate cancer and have a porrer overall prognosis.

6 Claims, No Drawings

PUBLICATIONS

Tennant, et al., "Changes in Insulin–Like Growth Factor System in Prostate Cancer," J. Investigative Medicine, 44(1): 154A (1996) Abstract Only.

Miglietta et al., "Suramin and Serum Insulin–Like Growth factor Levels in Metastatic Cancer Patients," Anticancer Research, 13:2473–2476 (1993).

Ware, "Growth Factors and Their Receptors as Determinants in the Proliferation and Metastasis of Human Prostate Cancer," Cancer and Metastasis Reviews, 12: 287–301 (1993).

Hsing, et al., "Regulation of Apoptosis Induced by Transforming Growth Factor–Beta 1 in Nontumorogenic Rate Prostatic Epithelial Cell Lines," Cancer Research, 56(22): 5146–5149 (1996) Abstract Only.

Culig et al., "Androgen Receptor Activation in Prostatic Tumor Cell Lines by Insulin–Like Growth Factor–I, Keratinocyte Growth Factor, and Epidermal Growth Factor," Cancer Research, 54(20): 5474–5478 (1994) Abstract Only.

Cohen et al., "The IGF Axis in the Prostate," Hormone Metab. Research, 26(2): 81–84 (1994) Abstract Only.

Iwamura et al., "Insulin–Like Growth Factor I: Action and Receptor Characterization in Human Prostate cancer Cell Lines," Prostate, 22(3): 243–252 (1993) Abstract Only.

Cohen et al., "Insulin–Like Growth Factors (IGFs), IGF Receptors, and IGF–Binding Proteins in Primary Cultures of Prostate Epithelial Cells," J. Clinical Endocrin. Metabl., 73(2): 401–407 (1991) Abstract Only.

Cohen et al., "Prostate–Specific Antigen (PSA) in an Insulin–Like Growth Factor Binding Protein–3 Protease Found in Seminal Plasma," J. Clin. Metab., 75(4): 1046–1053 (1992) Abstract Only.

Huynh et al., "A Role for Insulin–Like Growth Factor Binding Protein 5 in the Antiproliferative Action of the Antiestrogen ICI 182780," Cell Growth Differentiation, 7(11): 1501–1506 (1996) Abstract Only.

"Final Report on the Aspirin Component of the Ongoing Physician's Heath Study Steering Committee of the Physician's Health Study Research Group," N. Eng. J. of Medicine, 321(3): 129–135 (1989) Abstract Only.

Gann et al., "Prospective Study of Sex Hormone Levels and Risk of Prostate Cancer," J. Natl. Cancer Instit., 88(16): 1118–1126 (1996) Abstract Only.

Gann et al., "A Prospective Evaluation of Plasma Prostate–Specific Antigen for Detection of Prostatic Cancer," JAMA, 273(4): 289–294 (1995) Abstract Only.

Giovannucci et al., "The CAG Repeat Within the Androgen Receptor Gene and Its Relationship to Prostate Cancer," Proc. Natl. Acad Sci USA, 94(15): 8272 (1997) Abstract Only.

Goodman–Gruen et al., "Epidemiology of Insulin–Like Growth Factor–I in Elderly Men and Women. The Rancho Bernardo Study," Am. J. Epidemiol., 146(4): 357 (1997) Abstract Only.

Andersson et al., "Body Size and Prostate Cancer: a 20–year Follow–up Study Among 135006 Swedish Construction Workers," J. Natl. Cancer Instit., 89(5):385–389 (1997) Abstract Only.

La Vecchia et al., "Height and Cancer Risk in a Network of Case–Control Studies From Northern Italy," Interrogatory. J. Cancer, 45(2):275–279 (1990) Abstract Only.

Hebert et al., "Adult Height and Incidence of Cancer in Male Physicians (United States)," Cancer Causes Control, 8(4): 591–597 (1997) Abstract Only.

Tibblin et al., "High Birthweight as a Predictor of Prostate Cancer Risk," Epidemiology, 6(4): 423–424 (1995) Abstract Only.

Lassarre et al., "Serum Insulin–Like Growth Factors and Insulin–Like Growth Factor Binding Proteins in the Human Fetus. Relationships With Growth in Normal Subjects and n Subjects With Intrauterine Growth Retardation," Pediatr Res., 29(3): 219–225 (1991) Abstract Only.

Boyle et al., "Geographical and Temporal Patters on Incidence and Mortality From Prostate Cancer," Urology, 46(3, Suppl.A): 47–55 (1995) Abstract Only.

Meredith, "Finding From Asia, Australia, Europe, and North American on Secular Change in Mean Height of Children, Youths, and Young Adults," Am. J. Phys. Anthropol., 44(2): 315–325 (1976) Abstract Only.

Aquilina et al., "Androgen Deprivation as a Strategy for Prostate Cancer Chemoprevention," J. Natl. Cancer Instit., 89(10): 689–696 (1997) Abstract Only.

Pollak et al., "Somastatin Analogue SMS 201–995 Reduces Serum IGF–I Levels in Patients With Neoplasms Potentially Dependent on IGF–1," Anticancer Research, 9(4): 889–891 (1989) Abstract Only.

Rudman et al., "Effects of Human Growth Hormone in Men Over 60 Years Old," N. Engl. J. Med., 323(1): 1–6 (1990) Abstract Only.

* cited by examiner

CIRCULATING INSULIN-LIKE GROWTH FACTOR-I AND PROSTATE CANCER RISK

This application claims the benefit of U.S. Provisional Patent Application, Serial No. 60/072,560 filed Jan. 21, 1998.

The invention was partially supported by a grant from the United States government under Grant No. 58684 awarded by the National Institute of Health. The U.S. government may have rights in the invention.

BACKGROUND

1. Field of the Invention

The present invention relates to a method for assessing the risk of developing prostate cancer in an individual. Increased risk for prostate cancer is correlated with high insulin-like growth factor status (IGF status). Specifically, the method involves measurement of IGF-I and/or insulin-like growth factor binding protein-3 (IGFBP-3) in a specimen. High levels of IGF and/or low levels of IGFBP correlate with increased risk of developing prostate cancer.

In an alternative embodiment, the method involves determining the IGF/PSA status of an individual wherein determination of IGF status is combined with a measurement of prostate specific antigen (PSA) levels. The IGF/PSA status provides an improved method of assessing the prognosis of existing prostate cancer.

Furthermore, novel treatment modalities are suggested by the discovery of the link between IGF-axis component levels and prostate cancer that involve modulating IGF-axis component levels.

2. Description of the Prior Art

Prostate adenocarcinoma accounts for the majority of malignancies in males over the age of 65. Yearly screening for prostate cancer is recommended after the age of 45. There has been considerable effort toward identifying suitable prostate cancer markers to assist in predicting, diagnosing and monitoring this disease.

Prostate specific antigen (PSA) is recognized as the most sensitive marker of prostatic adenocarcinoma (M. K. Brawer Cancer 71(suppl):899–905 (1993); J. E. Oesterling J. Urol. 145:907–23 (1991)). PSA is also recognized as a proven screening vehicle (P. H. Gann, et al. Amer. Med. Assoc. 273:289–94 (1995); W. J. Catalona, et al. J. Urol. 151:1283–90 (1994)). It has been the most sensitive front line test for identifying prostate gland-contained, and hence presumably curable, cancer. PSA has also been useful in detecting clinically significant tumors, as opposed to latent, indolent micro-carcinomas. Screening for PSA is even superior to the common office practice of digital rectal examination (DRE). For example, Labrie et al. (Clin. Invest. Med. 16:425–39 (1993)) showed that 97% of cancers detected at annual follow-up by DRE plus PSA testing were PSA-positive. Thus, only a minimal benefit accrues from including DRE in the medical evaluation.

Investigators have searched for other markers or indicators of prostate cancer, but to date PSA has been the most useful marker. No one has heretofor studied the association of IGF-axis components with prostate cancer.

Insulin-like growth factors (IGF-I and IGF-II) belong to family of peptides that mediate a broad spectrum of growth hormone-dependent as well as independent mitogenic and metabolic actions. Unlike most peptide hormones, IGFs in circulation and other physiological fluids are associated with a group of high affinity binding proteins (IGFBPs) that specifically bind and modulate their bioactivity at the cellular level. Under normal conditions about 95–98% or the IGF-I in human plasma is bound to IGFBPs. Six structurally homologous IGFBPs with distinct molecular size, hormonal control, and tissue expression and functions, have been identified (J. I. Jones, et al. Endocrinol. Reviews 16:3–34, (1995)). Most serum IGF-I circulates in a relatively stable ternary complex consisting of IGFBP-3 and a unique leucine-rich, acid-labile subunit (ALS). Less than one percent of IGF-I is estimated to exist in a "free" or unbound form.

The rate of cell proliferation is positively correlated with risk of transformation of certain epithelial cell types. S. M. Cohen and L. B. Ellwein. Science 249:1007 (1990); S. M. Cohen and L. B. Ellwein. Cancer Research 51:6493 (1991). IGFs have mitogenic and anti-apoptotic influences on normal and transformed prostate epithelial cells. A. Y. Hsing, K. Kadomatsu, M. J. Bonharn, D. Danielpour. Cancer Research 56:5146 (1996); Z. Culig, A. Hobisch, M. V. Cronauer, C. Radmayr, J. Trapman, A. Hittmair, G. Hartsch, B. Klocker. Cancer Research 54:5474 (1994); P. Cohen, D. M. Peehl, R. G. Rosenfeld. Hormone and Metabolic Research 26:81 (1994); M. Iwamura, P. M. Stuss, J. B. Casamento, A. T. Cockett. Prostate 22:243 (1993); P. Cohen, D. M. Peehl, G. Lamson, R. G. Rosenfeld. J. Clinical Endocrinology & Metabolism 73:401 (1991); R. Rajah, D. Valentino, and P. Cohen. J. Biol. Chem. 272:12181 (1997). Most circulating IGF-I originates in the liver, but IGF bioactivity in tissues is related not only to levels of circulating IGFs and IGFBPs, but also to local production of IGFs, IGFBPs, and IGFBP proteases. J. J. Jones and D. R. Clemmons. Endocrine Reviews 16:3 (1995). Person-to-person variability in levels of circulating IGF-I and IGFBP-3 (the major circulating IGFBP (J. J. Jones and D. R. Clemnmons. Endocrine Reviews 16:3 (1995) is considerable (A. Juul, P. Bang, N. T. Hertel, K. Main, P. Dalgaard, K. Jorgensen, J. Muller, K. Hall, N. E. Skakkebaek. J. Clinical Endocrinology & Metabolism 78:744 (1994); A. Juul, P. Dalgaard, W. F. Blum, P. Bang, K. Hall, K. F. Michaelsen, J. Muller, N. E. Skakkeback. J. Clinical Endocrinology & Metabolism 80:2534 (1995) and heterogeneity in serum IGF-I level appears to reflect heterogeneity in tissue IGF bioactivity. Acromegaly and growth hormone deficiency are examples where there are clear changes in tissues that are correlated with serum IGF-I level, implying a relationship between serum IGF-I level and tissue IGF-I bioactivity. Also, factors that decrease circulating IGF-I level also affect expression of genes in target organs for IGF-I action in a manner that decreases IGF bioactivity. For example, antiestrogens lower IGF-I level (M. Pollak, J. Constantino, C. Polyochronakos, S. Blauer, H. Guyda, C. Redrnond, B. Fisher, R. Margolese. JNCI 82:1693 (1990), but also increase IGFBP expression (H. Huynh, X. Yang, B. Deroo, M. Pollak. Cell Growth and Differentiation 7:1501 (1996); H. Huynh, X. Yang, M. Pollak. J Biol Chem 271:1016 (1996) and decrease IGF-I receptor expression (H. Huynh, T. Nickerson, M. Pollak. Clinical Cancer Research 2:2037 (1996) in cells that are targets for IGF-I action. No one has heretofore shown that markers relating to IGF-axis components can also be used as a risk marker for prostate cancer.

SUMMARY OF THE INVENTION

Abbreviations and Definitions

AAG—3—alpha-androstanediol glucuronide.

ALS—Acid Labile Subunit. A protein found in the 150 KDa ternary complex wherein most of the circulating IGF is found. ALS is sensitive to inactivation by acid.

Binary complex—A two part complex of IGFBP and ALS or IGFBP and IGF.

Body fluid—Any biological fluid, including but not limited to the following: serum, plasma, lymph fluid, synovial fluid, follicular fluid, seminal fluid, amniotic fluid, milk, mammary fluid, whole blood, urine, spinal fluid, saliva, sputum, tears, perspiration, mucus tissue culture medium, tissue extracts and cellular extracts. Preferably, the body fluid is blood, plasma, serum or seminal fluid.

DHT—Dihydrotestosterone.

GH—Growth hormone.

GHBP—GH binding protein.

IGF—Insulin-like Growth Factor.

IGF—axis components—Those components that modulate the IGF/GH cascades including GH, GHBP, GH receptor, IGF, IGF receptor, IGF proteases, IGFBP 1 through 6 and other IGFBPs, ALS, IGF proteases, IGF and GH receptor antagonists, and the like.

IGF—axis component modulating agent—also: IGF status modulating agents. Includes any agent whose intended effect is to influence the GH or IGF cascades. Agents include GH, GHBP, IGF, IGFBP, ALS, IGFBP complex, GH receptors, IGF receptors, antibodies or modulators of any of the preceding, receptor antagonists for GH or IGF, or any drug that acts to modulate the IGF status of an individual including somatostatin, somatostatin analogues, GH antagonists, IGF antagonist, IGFBP stimulator, and the like.

IGFBP—Any IGF binding protein, including IGFBP-1 to 6 and the heretofore unsequenced IGFBPs. Preferably, the IGFBP is IGFBP-3 in the context of the assay described herein.

IGFBP-3—The major circulating IGF binding protein.

IGFBP complex—This term is defined herein to include either the binary complex of IGFBP and ALS or IGF or the ternary complex of IGFBP and ALS and IGF.

IGF status—The IGF status of an individual is reflected in the levels of IGF-axis components. For example a high IGF status is reflected by high levels of IGF and stimulators of IGF activity and low levels of inhibitors of IGF activity such as IGFBP. The IGF status of an individual is now known to vary -either up or down-in in certain conditions involving the prostate, including but not limited to, prostate adenocarcinoma or benign prostatic hyperplasia.

IGF/PSA status—A combination of IGF status and PSA levels. Individuals with high IGF/PSA status are at risk for developing severe prostate cancer. A high IGF/PSA status is reflected by high IGF and PSA levels and low IGFBP levels.

RR—Relative risk.

Risk Index—A value indicating the risk of a patient for developing prostate disease or poor prognosis for patients with prostate disease. The risk index can be generated from data concerning the IGF-axis component levels in a patient, including IGF or IGFBP levels and/or the PSA levels of a patient.

SHBG—Sex hormone binding globulin.

T—Testosterone.

Ternary complex—The 150 KDa complex composed of IGF, IGFBP and ALS.

Treatment designed to influence IGF status—Includes any medical treatment whose intended effect is to influence the GH or IGF cascades. Treatments may include treatments with such agents as GH, GHBP, IGF, IGFBP, ALS, IGFBP complex, GH receptors, IGF receptors, antibodies or inhibitors of any of the preceding, receptor antagonists for GH or IGF, or any drug that acts to modulate the IGF-axis status of an individual. Individuals include both human and animals, such as pigs, cattle, sheep, goats, horses, poultry, cats, dogs, fish, etc.

The present invention relates to assays for measuring IGF-I levels and their use for predicting, diagnosing and monitoring prostate cancer. A strong consistent positive association between IGF-I and prostate cancer risk has been observed, especially with adjustment for IGFBP-3. High levels of IGF-I are predictive of increased risk for prostate cancers, whereas IGFBP has a protective effect. Additionally, the IGF or IGF/IGFBP assay can be combined with a test for PSA for improved ability to predict patient prognosis and monitor treatment. Further, these findings suggest that it is possible to treat prostate cancers with agents that modulate the IGF-axis components.

In the its broadest embodiment, a method of predicting increased risk of prostate cancer in an individual is provided. The method involves measuring the "IGF status" or concentration of IGF-axis components in a body fluid from an individual, wherein changes in the IGF status or concentration of IGF-axis components as compared to normal reference values indicates an increased risk for prostate cancer.

In one embodiment, the invention is a method of predicting increased risk of prostate cancer in an individual, comprising measuring the concentration of insulin-like growth factor (IGF-I) in a body fluid from an individual, wherein an elevated concentration of IGF-I above a reference range for IGF-I indicates an increased risk for prostate cancer.

In another embodiment, the invention is a method of predicting increased risk of prostate cancer in an individual. The method involves measuring the concentration of IGF-I and IGFBP in a specimen from an individual, wherein increased IGF-I and decreased IGFBP, as compared to a normal reference range value, indicates an increased risk for prostate cancer.

In yet another embodiment, the invention is a method of measuring the IGF/PSA status of an individual. High IGF and PSA levels and/or low IGFBP levels are indicative of individuals at risk for severe prostate cancer or who have prostate cancer with a poor prognosis.

A multivariate adjustment of the IGF-I concentration relative to the IGFBP-3 concentration provides an adjusted IGF-I level or "IGF status" which can be compared to an adjusted normal reference range value. An algorithm can be designed, by those with skill in the art of statistical analyses, which will allow the user to quickly calculate an adjusted IGF level or "IGF status" for use in making predictions or monitoring prostate disease. With additional patient data, generated similarly to the manner described herein, it will be possible to more accurately define normal reference range values for IGF status parameters. The algorithm and normal reference values can be used to generate a device that will allow the end user to input IGF, IGFBP and quickly and easily determine the IGF status or risk index of an individual. Similarly, it is possible to provide a device that indicates the IGF/PSA status of an individual.

Finally, the invention pertains to a method of treating prostate cancer, comprising administering an IGF-axis component modulating agent to an individual with prostate cancer.

DETAILED DESCRIPTION OF THE INVENTION

As used herein the term "prostate disease" includes diseases or disorders associated with pathologic conditions of the prostate, including, but not limited to prostate cancer or benign prostatic hyperplasia. The method of the present invention is most preferably used to determine the risk of an individual developing prostate cancer, diagnosing prostate cancer or assessing the progress of the cancer. Accordingly, the method of the present invention may be useful in predicting prostate cancer, differentiating cancer from other prostatic diseases.

A suitable specimen is collected from an individual. Suitable specimens include any body fluid or tissue known to contain IGF-axis components and/or PSA. Preferably, the specimen is blood, serum, plasma or seminal fluid. The specimen may be collected by venipuncture or capillary puncture, and the specimen collected into an appropriate container for receiving the specimen. Alternatively, the specimen may be placed onto filter paper.

The IGF-axis components and/or PSA can be measured by techniques well known to those skilled in the art, including, but not limited to immunoassays such as enzyme-linked immunosorbent assay (ELISA), enzyme immunoassay (EIA), fluorescence polarization immunoassay (FPIA), fluorescence immunoassay (FIA) and radioimmunoassay (RIA). The assays described in U.S. application Ser. Nos. 08/626,641, 08/643,830, 08/763,244 and 08/829,094 are particularly suitable and are incorporated herein by reference. Further, the concentrations of the IGF-axis components and/or PSA may, for example, be measured by test kits supplied by DIAGNOSTIC SYSTEMS LABORATORIES, INC., Webster, Tex., USA.

In a preferred embodiment, total IGF-I can be measured. In some cases, it may be advantageous to measure total, bound and/or free IGF-I. For example, suitable highly specific and simple non-competitive ELISAs for reliable determination of IGF-I (M. J. Khosravi, et al., 1996 *Clin. Chem.* 42:1147–54), IGFBP-3 (Khosravi J. et al. 1996 *Clin. Chem.* S6:234) and IGFBP-1 (M. J. Khosravi, et al. 1996 *Clin. Chem.* S6:171) have been described. The high affinity antibodies incorporated in these immunoassays have been selected for lack of cross-reactivity or interference by the closely related peptides or binding protein.

Additionally, IGFBPs can be used as an indicator of decreased risk for prostate cancer. Preferably, the binding protein is IGFBP-3 and total, complexed and/or free IGFBP-3 may be measured. In alternative embodiments, the other IGFBPs (such as, but not limited to IGFBP-1) may also be used to predict the risk of prostate cancer. Additionally, acid-labile subunit (ALS) may also be used to predict susceptibility to prostate cancer. The ALS may be total ALS, complexed and/or free ALS. Other IGF-axis components may also influence the risk of prostate cancer.

Men in the highest quartile of circulating IGF-I have a relative risk of prostate cancer of 4.32 (95 percent confidence interval (CI) 1.76–10.6) compared to men in the lowest quartile, and there was significant linear trend such that a 100 ng/ml increase in IGF-I level was associated with a doubling of risk (p=0.001). Furthermore, this association is evident among men with normal as well as elevated baseline prostate specific antigen (PSA) levels. These results indicate that circulating IGF-I is predictor of prostate cancer risk, and perhaps progression, and thus have implications for risk reduction and treatment strategies.

EXAMPLE 1

This example shows that a higher serum IGF-I level is related to higher risk of developing prostate cancer. In view of the direct and indirect growth inhibitory properties of IGFBP-3 (reviewed in Rechler, *M. Endocrinology* 138:2645–2647 (1997)), we also postulated that high levels of IGFBP-3 would be inversely related to risk.

We used a nested case-control study within the Physician's Health Study (The Physicians' Health Study began in 1982 as a randomized double-blinded placebo-controlled trial of beta-carotene and aspirin in 22,017 U.S. male physicians age 40–82) (Steering Committee of the Physicians' Health Study Research Group. *N. Eng. J. Med.* 321:129 (1989)). The study excluded men with a history of myocardial infarction, stroke, transient ischemic attacks, unstable angina, cancer (except for non-melanoma skin cancer), current renal or liver disease, peptic ulcer, gout, contraindication to use of aspirin, or current usage of aspirin, other platelet-active agents, or vitamin A supplements. Each participant supplied written informed consent and permission to review medical records, and the project has been continuously approved by the Institutional Review Board at Brigham and Women's Hospital in accord with federal regulations) to examine serum IGF-I, IGF-II, and IGFBP-3 levels in relation to prostate cancer risk. At baseline, the men aged 40 to 82 provided information via mailed-in questionnaires on personal history of disease, usage of aspirin, vitamins, smoking habits, blood pressure, cholesterol levels, height, weight, and diet. 14,916 (68%) of the randomized physicians also provided blood specimens in 1982 (Before randomization, the men were mailed blood kits with instructions to have their blood drawn into vacutainer tubes containing EDTA (anti-coagulant), to centrifuge them and to return the plasma in polypropylene cryopreservation vials by overnight pre-paid courier. Cold packs, provided with the kits, were used to keep specimens cool until receipt the following morning, when they were aliquotted and stored at –82 degrees C. No specimen thawed or warmed substantially during storage). Through 1992, over 99% of surviving participants completed annual questionnaires reporting morbidity events and vital status was ascertained for 100%.

Following a report of prostate cancer in the annual questionnaires, we obtained medical records and pathology reports which were reviewed by physicians in the End Points Committee. Stage at diagnosis, tumor grade, Gleason score, type of presentation (e.g. symptoms and screening rectal examination), prostate specific antigen (PSA) level immediately before treatment, and treatment method were determined from medical record review by physician investigators (The Whitmore-Jewett classification scheme was used to identify stage, and cases without pathological staging were considered indeterminate, unless there was evidence of metastases. "High grade/stage cancer" were those cases presenting as stage C or D, or stage A, B, or indeterminate with either poor histological differentiation or a Gleason score of seven or higher).

Cases and controls were selected from among the 14,916 physicians who provided blood. As of March 1992, after 10 years of follow-up we confirmed 520 cases of prostate cancer, of whom 152 cases had adequate sample volume for IGF assays in 1997. Circulating steroid hormone levels P. H. Gann, C. H. Hennekens, J. Ma, C. Longcope, M. J. Stampfer, *JNCI* 88:1118 (1996). PSA (P. H. Gann, C. H. Hennekens, M. J. Stampfer, *JAMA* 273:289 (1995), and CAG polymorphisms of the androgen receptor gene (E. Giovannucci, M. J. Stampfer, K. Krithivas, M. Brown, A. Brufsky, J. Talcott, C. H. Hennekens, P. W. Kantoff. *Proc. Natl. Acad. Sci. USA* 94:3320 (1997) had previously been measured in these cases from the same blood samples originally collected in 1982 (Selection bias is minimal here as it is unlikely that subjects returned blood samples or provided adequate blood volume differentially based on any relation between their IGF levels in 1982 and later development of prostate cancer. Previous study has shown that cases who did and did not provide blood samples were not appreciably different in their baseline lifestyle characteristics (P. H. Gann, C. H. Hennekens, M. J. Stampfer, *JAMA* 273:289 (1995). All assays reported in this study are from blood specimens collected, on average, seven years (min.=6 months, max.=9.5 years) prior to clinical diagnosis of prostate cancer.

We selected controls at random from those men who provided blood and who had not reported a diagnosis of prostate cancer up to the date of diagnosis of the case. We excluded those men without adequate blood sample volume and those who had total or partial prostatectomies by the time of the case diagnosis because they may not have been fully at risk for the disease when the cases were diagnosed. We matched one control to each case based on smoking status (never, past, or current smoker), duration of follow-up, and age within one year.

IGF-I, IGF-II, and IGFBP-3 were assayed using ELISAs with reagents from DIAGNOSTIC SYSTEMS LABORATORY INC. (DSL Inc., Webster, Tex.) (This methodology was selected as it was shown to be more reproducible and more appropriate for large numbers of samples than an RIA technique we previously employed (M. Pollak, J. Constantino, C. Polyochronakos, S. Blauer, H. Guyda, C. Redmond, B. Fisher, R. Margolese. *JNCI* 82:1693 (1990). The IGF-I values obtained by the ELISA were highly correlated (Pearson r=0.97) with values obtained by RIA following acid chromatography. All assays were carried out in a blinded fashion and quality control samples were embedded within assay runs. Average intra-assay coefficients of variation for IGF-I and IGF-II were 4.9% and 3.0%, respectively. The IGFBP-3 assay employed does not cross-react with other IGF binding proteins. Experiments with recombinant IGF-I and IGFBP-3 confirm that the assay detects IGFBP-3 whether or not it is complexed to IGF-I in the presence or absence of the acid labile subunit. The average intra-assay coefficient of variation for IGFBP-3 was 9.0%. To evaluate the effect of our blood collection methods on IGF-I levels, we compared IGF-I and IGFBP-3 levels in blood samples which were processed and serum frozen immediately after venipuncture (the usual collection and processing methods) to samples, which were stored as heparinized whole blood for 24 and 36 hours before processing (mimicking our collection conditions). The mean IGF-I and IGFBP-3 values were almost identical and the interclass correlations between results of the two collection methods were 0.98 for IGF-I and 0.96 for IGFBP-3, indicating that our collection methods did not adversely affect sample integrity. It has been shown that s single IGF-I measurement is representative of levels over time (To examine how well a single measurement of IGF-I represents levels overtime, we collected two blood samples each from 16 people, eight weeks apart (time 1 and time 2). The correlation between blood levels taken at time 1 and time 2 was 0.65; D. Goodman-Gruen, E. Barrett-Connor. *Amer. J. Epidemiol.* 145:970 (1997).

Paired t-tests were used to compare the means of IGF-I, IGF-II, and IGFBP-3 between cases and controls. We then examined the age-standardized (using five groups, 40–50, 51–55, 56–60, 61–65, 66–80) mean values of various predictors for prostate cancer within quartiles of IGF-I among the controls. Conditional logistic regression was used to analyze the associations between IGF and prostate cancer adjusting for other possible risk factors for prostate cancer—PSA, height, weight, body mass index, CAG polymorphisms of the androgen receptor gene, and plasma androgen levels, including estrogren, testosterone (T), dihydrotestosterone (DHT), sex hormone binding globulin (SHBG), prolactin, and 3-alpha-androstanediol glucuronide (AAG) (P. H. Gann, C. H. Hennekens, J. Ma, C. Longcope, M. J. Stampfer, *JNCI* 88:1118 (1996); P. H. Gann, C. H. Hennekens, M. J. Stampfer, *JAMA* 273:289 (1995); E. Giovannucci, M. J. Stampfer, K. Krithivas, M. Brown, A. Brufsky, J. Talcott, C. H. Hennekens, P. W. Kantoff. *Proc. Natl. Acad. Sci. USA* 94:3320 (1997). E. Giovannucci, E. B. Rimm, M. J. Stampfer, G. A. Colditz, W. C. Willett. *Cancer Epidemiology Biomarker, and Prevention* (in press); S-O Andersson, A. Wolk, R. Bergstrom, H-O Adami, G. Engholm, A. Englund, O. Nyren. *JNCI* 89:385 (1997); B. MacMahon and D. Trichopolous. *Epidemiology Principles & Methods* (Little, Brown & Company, Boston, Mass. 1996), pp. 287–91; and K. Rothman. *Modern Epidemiology* (Little, Brown & Company, Boston, NIA 1986), pp. 250–7.

Because we hypothesized that IGFBP-3 reduces the bioactivity of IGFs, we simultaneously adjusted for levels of both IGFs and IGFBP-3. We estimated relative risk (RR) from the odds ratios and computed 95 percent confidence intervals (CI) (K. Rothman. *Modern Epidemiology* (Little, Brown & Company, Boston, NIA 1986), pp. 250–7. In some analyses, we used unconditional logistic regression models and adjusted for age (eight five-year categories) and smoking (never, past, and current) in the models to make full use of the data without restriction to the matched pairs. D. G. Kleinbaum, L. L. Kupper, and H. Morgenstern. *Epidemiologic Research* (Van Nostrand Reinhold, Boston, Mass. 1982), pp. 433–43. We repeated the basic analyses examining only the high grade/stage cases, only low grade/stage cases, and only cases occurring after the first five years of follow-up, as prior studies have shown that some risk factors for prostate cancer are stronger for high grade/stage tumors P. H. Gann, C. H. Hennekens, J. Ma, C. Longcope, M. J. Stampfer, *JNCI* 88:1118 (1996); E. Giovannucci, M. J. Stampfer, K. Krithivas, M. Brown, A. Brufsky, J. Talcott, C. H. Hennekens, P. W. Kantoff. *Proc. Natl. Acad. Sci. USA* 94:3320 (1997). We examined IGF-I and prostate cancer within age groups (<=60, >60 at baseline) and smoking categories (never, past, current) to consider potential interactions.

All exposures of interest and covariates, with the exceptions of age and smoking, were analyzed in quartile groups with the lowest quartile as the reference category. We tested linear trends for statistical significance by assigning the medians of each quartile as scores. B. Rosner. *Fundamentals of Biostatistics* (Duxbury Press, Boston, Mass. 1995), pp. 604–7.

The mean level of IGF-I among the cases (269.4 ng/ml) was significantly higher than among controls (248.9 ng/ml) (p=0.03). Means of IGF-II and IGFBP-3 were similar among cases and controls (p=0.85 and 0.95 respectively). Table 1 presents age-standardized means of IGF-II, IGFBP-3, estradiol, T, DHT, SHBG, lycopene, weight, height, body mass index, and medians of PSA among 152 controls, within quartiles of IGF-I. PSA and estradiol had weak positive associations with IGF-I levels, while there was some suggestion that lycopene levels were lower among men in the highest quartile of IGF-I. There was no significant correlation between IGF-I and any of these factors except IGF-II (r=0.5) and IGFBP-3 (r=0.6).

TABLE 1

Age-standardized characteristics among 152 controls within quartiles of IGF-I*

| | IGF Quartile | | | |
|---|---|---|---|---|
| | 1 | 2 | 3 | 4 |
| IGF-I (ng/ml) | 99.4–184.8 | 184.9–236.95 | 236.96–293.75 | 293.76–499.6 |
| n | 38 | 38 | 38 | 38 |
| Age, years (mean) | 63.9 | 58.9 | 59.0 | 59.3 |
| IGF-II, ng/ml (mean) | 418 | 536 | 509 | 583 |
| IGFBP-3, ng/ml (mean) | 2234 | 2841 | 2829 | 3473 |
| PSA+, ng/ml (median) | 2.19 | 2.27 | 2.81 | 2.49 |
| Lycopene, ng/ml (mean) | 445 | 430 | 438 | 388 |
| Estradiol, ng/ml (mean) | 35.9 | 37.2 | 38.6 | 39.4 |
| Testosterone, ng/ml (mean) | 5.27 | 4.74 | 5.28 | 5.60 |
| DHT+, ng/ml (mean) | 0.41 | 0.41 | 0.44 | 0.43 |
| SHBG+, nmol/L (mean) | 27.9 | 20.9 | 24.8 | 21.7 |
| Weight, kg (mean) | 77.1 | 78.6 | 78.7 | 77.4 |
| Height, m (mean) | 1.77 | 1.76 | 1.77 | 1.76 |
| BMI+, kg/m$^2$ (mean) | 24.7 | 25.4 | 25.0 | 24.9 |

*Standardized using 5 categories of age (40–50, 51–55, 56–60, 61–65, 66–80).
+PSA = prostate specific antigen,
DHT = dihydrotestosterone,
SHBG = sex hormone binding globulin,
BMI = body mass index.

IGF-I was significantly associated with prostate cancer risk in a univariate analysis; men in the highest quartile had a relative risk of 2.41 (95 percent CI 1.23–4.74) as compared to men in the lowest quartile (Table 2). With further adjustment for IGFBP-3, these men had more than four times the risk of prostate cancer compared to the reference group (RR=4.32, 95 percent CI 1.76–10.6). IGF-II and IGFBP-3 were not associated with prostate cancer risk when examined individually, but IGFBP-3 was inversely associated with risk after controlling for IGF-I (RR for fourth vs. first quartile 0.41, 95 percent CI 0.17–1.03). There was a significant linear trend between IGF-I and prostate cancer risk, especially after adjusting for IGFBP-3; a 100 ng/ml increase in IGF-I corresponded to an approximate doubling of risk (RR=2.09 per 100 ng/ml increase, 95 percent CI 1.35–3.22). As anticipated, it was important to consider the combined effects of IGF-I and IGFBP-3 simultaneously, and these were examined together in subsequent analyses.

TABLE 2

Relative risk of prostate cancer according to quartiles of IGF-I, IGF-II, IGFBP-3.

| | Quartiles | | | | Trend |
|---|---|---|---|---|---|
| | 1 | 2 | 3 | 4 | p-value |
| RR associated with IGF-I Quartiles | | | | | |
| IGF-I* | 1.00 | 1.32 (0.62–2.80)+ | 1.81 (0.92–3.56) | 2.41 (1.23–4.74) | 0.01 |
| IGF-II | 1.00 | 1.00 (0.54–1.84) | 0.67 (0.33–1.37) | 0.97 (0.48–1.95) | 0.74 |
| IGFBP-3 | 1.00 | 0.92 (0.48–1.79) | 0.69 (0.33–1.44) | 1.07 (0.54–2.11) | 0.96 |
| Simultaneous adjustment for IGF-I or IGFBP-3 | | | | | |
| IGF-I | 1.00 | 1.94 (0.83–4.56) | 2.83 (1.27–6.28) | 4.32 (1.76–10.6) | 0.001 |
| IGFBP-3 | 1.00 | 0.50 (0.23–1.10) | 0.33 (0.14–0.82) | 0.41 (0.17–1.03) | 0.09 |

*n = 151 for cases, 1 case missing of IGF-I.
+95% confidence intervals
Test for linear trend calculated by assigning the medians of the quartiles as scores.

IGF-I remained a significant independent predictor of prostate cancer risk even after inclusion of quartiles of weight, height, body mass index, androgen receptor CAG repeats, and various circulating hormone levels (estradiol, T, DHT, SHBG, prolactin, and AAG) in the multivariate models. Adding quartiles of PSA to the model attenuated the association for IGF-I slightly, though the results remained significant (RR=3.31, 95 percent CI 1.09–10.1 for the fourth vs. first quartile, adjusting for IGFBP-3).

To investigate whether the observed associations between IGF-I and prostate cancer could be due to increased IGF-I levels among pre-clinical undiagnosed cases in 1982, we repeated the basic analyses including only those men who were diagnosed five years or more after the start of follow-up. With the remaining 125 cases and 152 controls, we observed very similar results to previous analyses based on all cases and controls, and the effect of IGF-I adjusted for PSA was also unaffected.

We compared the potential association between IGF-I and prostate cancer risk among men with high grade/stage vs. low grade/stage cancer at diagnosis and observed no significant difference (RR for the fourth vs. first quartile of IGF-I 3.40 (95 percent CI 1.14–10.1) for high grade/stage cancers and 5.46 (95 percent CI 1.93–15.5) for low grade/stage cancers), suggesting that IGF-I does not differentially influence the development of high vs. low grade/stage tumors.

When we stratified subjects by the median case baseline age of 60, the increased risk associated with IGF-I was stronger among the older men. Men over the age of 60 and in the highest quartile of IGF-I had a RR of 7.93 (95 percent CI 2.05–30.7), adjusting for IGFBP-3, compared to men of similar age in the lowest quartile, and we found no association between quartiles of IGF-I and risk among the men age 60 or less. Among both older and younger men, however, there was a significant linear relationship between RR and IGF-I level (RR=1.83 per 100 ng/ml increase in IGF-I, p=0.047 for younger men; RR=2.55 per 100 ng/ml increase in IGF-I, p=0.006 for older men). We also examined IGF-I within strata of smoking and within strata of six plasma androgens but observed no evidence of interaction.

EXAMPLE 2

As PSA acts as an IGFBP protease in prostatic issue (P. Cohen, H. C. Graves, D. M. Peehl, M. Kamarei, L. C.

Biudice, R. G. Rosenfeld. *J. Clinical Endocrinology & Metabolism* 75:1046 (1992), we also investigated possible interactions involving PSA. There was no significant correlation between circulating PSA and circulating IGFBP-3, consistent with the view that PSA is enzymatically inert in the circulation. We classified men by quartile of IGF-I and low (≦4 ng/ml) vs. high (>4 ng/ml) PSA level, creating eight mutually exclusive categories of IGF-I and PSA. The low-PSA/lowest quartile of IGF-I category was used as the reference group. Similar methods were used to examine potential interactions between IGF-I and plasma androgens (using the median among controls as the cutpoint for low and high androgen levels).

Data in Table 3 confirm that as expected, men with elevated baseline PSA were more likely to be subsequently diagnosed with prostate cancer than those with PSA less than 4 ng/ml. More importantly, serum IGF-I level was strongly related to risk of developing prostate cancer even among men with a baseline PSA less than 4 ng/ml (multivariate RR of clinical diagnosis during follow-up increased from 1.00 to 4.57 across quartiles of IGF-I, adjusted for IGFBP-3 and age, and smoking). Furthermore, assuming that men with PSA greater than 4 ng/ml have a high likelihood of harboring occult prostate cancer (P. H. Gann, C. H. Hennekens, M. J. Stampfer, *JAMA* 273:289 (1995), the data provide evidence for a substantial influence of IGF-I on the natural history of clinically occult prostate cancer (multivariate RR of clinical diagnosis during follow-up increased from 3.92 to 17.5 across quartiles of IGF-I among men with elevated baseline PSA). These results suggest men in the highest quartile of IGF-I have four and a half times greater risk of prostate cancer than men in the lowest quartile regardless of their PSA levels, and that a combined assessment of IGF-I level and PSA may better predict subsequent prostate cancer than a PSA measure alone.

TABLE 3

IGF-I and risk of prostate cancer by category of pre-diagnostic PSA level.

| PSA level | RR* associated with IGF-I quartile | | | |
| --- | --- | --- | --- | --- |
| | 1 | 2 | 3 | 4 |
| ≦4 ng/ml | 1.00+ | 1.66 | 2.07 | 4.57 |
| | — | (0.70–3.92) | (0.84–5.09) | (1.79–11.6) |
| >4 ng/ml | 3.92 | 11 | 16 | 17.5 |
| | (1.01–15.3) | (1.84–65.4) | (4.08–62.6) | (3.83–80.1) |

*Multivariate RR adjusted for age (40–44, 45–49, 50–54, 55–59, 60–64, 65–69, 70–74, 75–80), smoking (never, past, current), and IGFBP-3 (quartiles)
+Reference group Our data support the hypothesis that higher circulating IGF-I levels are associated with higher rates of malignancy in the prostate gland. Alternative explanations for the observations in this study include measurement error, bias, and chance C. H. Hennekens and J. E. Buring. *Epidemiology in Medicine* (Little, Brown & Company, Boston, Mass. 1987), p. 243. We measured circulating adult levels of IGF-I and IGFBP-3 using a single blood sample drawn, on average, seven years prior to cancer diagnosis. It is possible that another measure of IGF-I physiology (i.e. adolescent or early adulthood mean IGF-I assessed over time, tissue IGF bioactivity, or rate of cell turnover in the prostate gland) would better capture the true etiologically relevant variable. To the extent that our single measurement is a proxy for such a variable and that the measurement errors are non-systematic and proportionately equal among cases and controls, we have reduced the observable variation between our cases and controls, and our results are likely to underestimate the true association between IGF-I and prostate cancer risk. K. Rothman. *Ibid.* pp. 84–9. Measurement error in assessing prostate cancer outcome is minimal given the physician study base and the histologic confirmation of all cases, although there may be some under-ascertainment of existing cases which would also lead to an underestimation of effect.

A small case-control study (n=52 cases), in which blood samples were drawn from men already diagnosed with prostate cancer and healthy controls, showed a positive association of borderline significance between IGF-I level and prostate cancer risk In a small study (n=52), using blood samples collected post-diagnosis, the authors reported a borderline significant association between IGF-I and prostate cancer risk (RR=1.91, 95 percent CI 1.00–3.73 per 60 ng/ml increment of IGF-I, adjusted for age, height, body mass index, years of schooling, SHBG, T, estradiol, DHT, and dehydroepiandrosterone sulfate). C. S. Mantzoros, A. Tzonou, L. B. Signorello, M. Stampfer, D. Trichopoulos, H-O Adami. *British J. of Cancer* (in press). However, the retrospective design used in that study could not rule out an effect of the cancer, or its treatment, on IGF-I levels.

The association between circulating IGF-I level and risk of prostate cancer is stronger than that of any previously reported risk factor, including steroid hormone levels (P. H. Gann, C. H. Hennekens, J. Ma, C. Longcope, M. J. Stampfer, *JNCI* 88:1118 (1996), or anthropomorphic variables (E. Giovannucci, E. B. Rimm, M. J. Stampfer, G. A. Colditz, W. C. Willett. *Cancer Epidemiology Biomarker, and Prevention* (in press); S-O Andersson, A. Wolk, R. Bergstrom, H-O Adami, G. Engholm, A. Englund, O. Nyren. *JNCI* 89:385 (1997); C. La Vecchia, E. Negri, F. Parazzini, P. Boyle, B. D'Avanzo, F. Levi, A. Gentile, S. Franceschi. *Intl. J. Cancer* 45:275 (1990); P. Hebert, U. Ajani, N. R. Cook, I-M. Lee, K. S. Chan, C. H. Hennekens. *Cancer Causes & Control* 8:591 (1997); G. Tibblin, M. Eriksson, S. Cnattingius, A. Ekbom. *Epidemiology* 6:423 (1995). Prior reports showing a weak relationship between prostate cancer risk and height (C. La Vecchia, E. Negri, F. Parazzini, P. Boyle, B. D'Avanzo, F. Levi, A. Gentile, S. Franceschi. *Intl. J. Cancer* 45:275 (1990); P. Hebert, U. Ajani, N. R. Cook, I-M. Lee, K. S. Chan, C. H. Hennekens. *Cancer Causes & Control* 8:591 (1997), are of particular interest in the context of our results, as IGF-I levels have been reported to be correlated with height (A. Juul, P. Bang, N. T. Hertel, K. Main, P. Dalgaard, K. Jorgensen, J. Muller, K. Hall, N. E. Skakkebaek. *J. Clinical Endocrinology & Metabolism* 78:744 (1994), and height may act as a weak surrogate for IGF-I. Circulating IGF-I level, in turn, may be related to risk because it represents a determinant of and/or a surrogate for prostate tissue IGF bioactivity and/or cellular proliferation rate.

In our study population, height was moderately associated with prostate cancer risk, independent of weight, age, smoking, IGF-I, and IGFBP-3 (RR=1.05 per cm increase in height, p=0.05). However, we did not observe an association between IGF or IGFBP-3 and height in this study, possibly due to small sample size or older age of the subjects. A small study (n=21 cases) that reported high birth weight to be associated with a higher incidence of prostate cancer, (G. Tibblin, M. Eriksson, S. Cnattingius, A. Ekbom. *Epidemiology* 6:423 (1995), may also be consistent with our observations, as there is evidence that birth weight is positively correlated with IGF-I level (C. Lassarre, S. Hardouin, F. Daffos, F. Forestier, F. Frankenne, M. Binoux. *Pediatric Research* 29:219 (1991).

Age-standardized prostate cancer incidence is increasing even allowing for changes in ascertainment (P. Boyle, P. Maisonneuve, P. Napalkow. *Urology* 46:47 (1995). There are grounds for speculation that in certain human populations there is a trend towards increasing IGF-I levels. The physiological basis for the secular trend towards increased height over the past few generations (H. Meredith. *Am. J. Phys. Anthropol.* 44:315 (1976), remains unexplained, but this may be correlated with increased IGF-I levels, particularly as severe malnutrition is less common, and malnutrition is known to reduce IGF-I level (J. P. Thissen, J. M. Keteislegen, L. B. Underwood. *Endocrine Reviews* 15:80 (1994).

Until now, reduction of androgen action has been the principal strategy under investigation for prostate cancer prevention (J. W. Aquilina, J. J. Lipsky, D. G. Bostwick. *JNCI* 89:689 (1997). Our data suggest that the HG/IGF-axis may also deserve attention in this context. Reduction of IGF-I levels by lifestyle modifications may not be possible, as a recent cross-sectional study found IGF-I to be positively correlated with younger age, male gender, and alcohol intake, but uncorrelated with lifestyle-related factors such as body fat, lean body mass, current smoking, physical activity, and use of common medications (D. Goodman-Gruen, E. Barrett-Connor. *Amer. J. Epidemiol.* 145:970 (1997). However, pharmacological approaches to decreasing IGF-I levels deserve investigation as risk reduction strategies specifically targeted to those men who have elevated risk defined on the basis of high IGF-I level.

The data also provide a rationale for examining the use of this strategy in the treatment of early prostate cancer. Currently, IGF-I levels may be reduced by the use of somatostatin analogues (M. Pollak, C. Polchronakos, H. Guyda. *Anticancer Research* 9:889 (1989), or growth hormone releasing hormnone antagonists (M. Zarandi, J. E. Horvath, G. Halmos, J. Pinski, A. Nagy, K. Groot, Z. Rekasi, A. V. Schally. *Proc. Natl. Acad. Sci. USA* 91:12298 (1994). The former are well-tolerated agents commonly used in treatment of acromegaly and are under investigation in other trials (M. Pollak, J. Ingle, V. Suman, J. Kugler. Rationale for combined antiestrogensomatostatin analogue therapy of breast cancer. In Salmon, S. (Ed) *Adjuvant Therapy of Cancer VIII*, p. 145–153, Lippincott, Philadelphia, 1997). In contrast, our results raise concern that administration of growth hormone or IGF-I over long periods, proposed for elderly men (D. Rudman, A. G. Feller, H. S. Nagraj, G. A. Gorgans, P. Y. Lalitha, A. F. Goldberg, R. A. Schlenker, L. Cohn, I. W. Rudmam, D. E. Mattson. *NEJM* 323:1 (1990), may increase risk of prostate cancer.

The data reported here justify further epidemiological and biological investigation of IGF-I and IGFBP-3 as predictors of prostate cancer risk, as candidate intermediate endpoints for chemoprevention studies, and as targets for future prevention and therapeutic strategies.

What is claimed is:

1. A method of predicting an increased risk for prostate cancer, comprising:
    a) measuring the concentration of IGF-I in a body fluid from each individual of a reference group of healthy individuals without prostate cancer to establish a reference level;
    b) measuring the concentration of IGF-I in a body fluid from an individual; and
    c) comparing the concentration of ICF-I in the individual to the reference level, wherein an elevated concentration of IGF-I of 100 ng/ml above the reference level indicates a doubling of the risk for prostate cancer.

2. The method of claim 1, wherein said body fluid is blood, plasma, or serum.

3. The method of claim 1, wherein said IGF-I is total IGF-I,free IGF-I, or complexed IGF-I.

4. A method of predicting increased risk of prostate cancer in an individual, comprising:
    a) measuring the concentration of ICF-I in a body fluid from the individual;
    b) comparing the individual's IGf-I concentration to a concentration of a prostate cancer free control group, wherein an elevated concentration of IGF-I of 100 ng/ml above the control concentration indicates a doubling of the risk for prostate cancer.

5. The method of claim 4, wherein said body fluid is blood, plasma, or serum.

6. The method of claim 4, wherein said IGF-I is total IGF-I, free IGF-I, or complexed IGF-I.

* * * * *

UNITED STATES PATENT AND TRADEMARK OFFICE
CERTIFICATE OF CORRECTION

PATENT NO.      : 6,410,335 B1
DATED           : June 25, 2002
INVENTOR(S)     : Michael N. Pollak et al.

It is certified that error appears in the above-identified patent and that said Letters Patent is hereby corrected as shown below:

Title page,
Item [73], Assignee, replace "The Brigham and Woman's Hospital, Inc." with
-- "The Brigham and Woman's Hospital, Inc." --

Column 14,
Line 21, replace "ICF-I" with -- IGF-I" --
Line 28, replace "IGF-I,free" with -- "IGF-I, free" --
Line 31, replace "ICF-I" with -- "IGF-I" --
Line 33, replace "IGf-I" with -- "IGF-I" --

Signed and Sealed this

Fourth Day of March, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,410,335 B1
DATED : June 25, 2002
INVENTOR(S) : Michael N. Pollak et al.

It is certified that error appears in the above-identified patent and that said Letters Patent is hereby corrected as shown below:

<u>Title page,</u>
Item [73], Assignee, replace "The Brigham and Woman's Hospital, Inc." with
-- "The Brigham and Women's Hospital, Inc." --

<u>Column 14,</u>
Line 21, replace "ICF-I" with -- IGF-I" --
Line 28, replace "IGF-I,free" with -- "IGF-I, free" --
Line 31, replace "ICF-I" with -- "IGF-I" --
Line 33, replace "IGf-I" with -- "IGF-I" --

This certificate supersedes Certificate of Correction issued March 4, 2003.

Signed and Sealed this

Fifteenth Day of April, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,410,335 B1
DATED : June 25, 2002
INVENTOR(S) : Pollak et al.

It is certified that error appears in the above-identified patent and that said Letters Patent is hereby corrected as shown below:

<u>Title page,</u>
Item [73], Assignees, replace "Sir Mortimer B. Davis - Jewish General Hospital Foundation, Montreal, (CA)" with -- Lady Davis Institute, Montreal (CA) --

Signed and Sealed this

Tenth Day of February, 2004

JON W. DUDAS
*Acting Director of the United States Patent and Trademark Office*